United States Patent
McNair

(10) Patent No.: US 12,020,820 B1
(45) Date of Patent: Jun. 25, 2024

(54) PREDICTING SPHINGOLIPIDOSES (FABRY'S DISEASE) AND DECISION SUPPORT

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 1439 days.

(21) Appl. No.: 15/912,258

(22) Filed: Mar. 5, 2018

Related U.S. Application Data

(60) Provisional application No. 62/466,367, filed on Mar. 3, 2017.

(51) Int. Cl.
*G16H 50/30* (2018.01)
*G06N 7/01* (2023.01)
*G06N 20/00* (2019.01)
*G16H 50/20* (2018.01)
(Continued)

(52) U.S. Cl.
CPC .............. *G16H 50/30* (2018.01); *G06N 7/01* (2023.01); *G06N 20/00* (2019.01); *G16H 50/20* (2018.01); *G16H 50/50* (2018.01); *G16H 50/70* (2018.01); *G01N 2800/044* (2013.01);
(Continued)

(58) Field of Classification Search
CPC ........ G16H 50/20; G16H 50/30; G16H 50/50; G16H 50/70; G01N 2800/044; G01N 2800/50
See application file for complete search history.

(56) References Cited

U.S. PATENT DOCUMENTS

| 5,804,405 A | 9/1998 | Ahlfors |
| 6,129,664 A | 10/2000 | Macfarlane et al. |
| 6,759,189 B1 | 7/2004 | Meikle et al. |

(Continued)

FOREIGN PATENT DOCUMENTS

| EP | 2024745 A2 | 2/2009 | |
| EP | 2365458 A2 * | 9/2011 | ........... G06F 19/322 |

(Continued)

OTHER PUBLICATIONS

Ramaswami, Uma, et al. "Measuring patient experiences in Fabry disease: validation of the Fabry-specific Pediatric Health and Pain Questionnaire (FPHPQ)." Health and Quality of Life Outcomes 10.1 (2012): 1-9. (Year: 2012).*

(Continued)

*Primary Examiner* — Mamon Obeid
*Assistant Examiner* — Chance L Smith
(74) *Attorney, Agent, or Firm* — Invoke

(57) ABSTRACT

A diagnostic and decision support technology is provided for determining the presence, identity, and/or severity of an inherited lysosomal storage disorder. In particular, a mechanism is provided to detect and classify a lysosomal storage disorder in a human patient, which utilizes a logistic regression classifier determined based on a multi-variable-composite-biomarker comprising a specific set of physiological variables of the patient. This multi-variable statistical predictive biomarker approach may be employed for identifying persons whose attributes are consistent with features of sphingolipidoses, such as Fabry's Disease.

22 Claims, 8 Drawing Sheets

(51) Int. Cl.
*G16H 50/50* (2018.01)
*G16H 50/70* (2018.01)
(52) U.S. Cl.
CPC ... *G01N 2800/285* (2013.01); *G01N 2800/50* (2013.01); *G01N 2800/60* (2013.01)

(56) References Cited

U.S. PATENT DOCUMENTS

| | | | |
|---|---|---|---|
| 7,361,481 | B2 | 4/2008 | Meikle et al. |
| 7,378,231 | B1 | 5/2008 | Meikle et al. |
| 7,662,558 | B2 | 2/2010 | Liew |
| 7,951,545 | B2 | 5/2011 | Okamura et al. |
| 8,003,337 | B2 | 8/2011 | Okamura et al. |
| 8,101,358 | B2 | 1/2012 | Liew |
| 8,232,073 | B2 | 7/2012 | Crawford et al. |
| 8,410,101 | B2 | 4/2013 | Schiffmann et al. |
| 8,569,001 | B2 | 10/2013 | Okamura et al. |
| 8,592,140 | B2 | 11/2013 | Crawford et al. |
| 8,771,974 | B2 | 7/2014 | Crawford et al. |
| 8,809,009 | B2 | 8/2014 | Crawford et al. |
| 9,222,120 | B2 | 12/2015 | Crawford et al. |
| 9,340,822 | B2 | 5/2016 | Crawford et al. |
| 9,495,514 | B2 | 11/2016 | McNair |
| 9,495,515 | B1 * | 11/2016 | Kennedy ............ G16B 40/00 |
| 2005/0262031 | A1 * | 11/2005 | Saidi .................. G16Z 99/00 600/407 |
| 2006/0172429 | A1 | 8/2006 | Nilsson et al. |
| 2007/0077553 | A1 | 4/2007 | Bentwich |
| 2007/0118410 | A1 | 5/2007 | Nadai |
| 2008/0056994 | A1 | 3/2008 | Kaneski et al. |
| 2009/0299645 | A1 | 12/2009 | Colby et al. |
| 2010/0047844 | A1 | 2/2010 | Aerts |
| 2010/0062948 | A1 | 3/2010 | Kleinfeld et al. |
| 2010/0174152 | A1 * | 7/2010 | McNair .............. G16H 10/20 600/301 |
| 2011/0093249 | A1 | 4/2011 | Holmes et al. |
| 2011/0212090 | A1 | 9/2011 | Pedersen et al. |
| 2013/0287772 | A1 | 10/2013 | Halbert et al. |
| 2013/0304392 | A1 | 11/2013 | Deciu et al. |
| 2015/0005189 | A1 | 1/2015 | Wong et al. |
| 2016/0160284 | A1 * | 6/2016 | Kassis ............ G01N 33/6896 435/7.1 |
| 2016/0178643 | A1 | 6/2016 | Everett et al. |
| 2018/0068083 | A1 | 3/2018 | Cohen et al. |
| 2019/0086324 | A1 | 3/2019 | Marrinucci et al. |
| 2019/0183869 | A1 * | 6/2019 | Castelli ................ A61K 31/45 |
| 2020/0155654 | A1 * | 5/2020 | Almon ................ A61P 3/00 |
| 2021/0110895 | A1 | 4/2021 | Shriberg et al. |
| 2021/0319899 | A1 | 10/2021 | Liu et al. |
| 2021/0353224 | A1 | 11/2021 | Etkin et al. |
| 2021/0358594 | A1 | 11/2021 | Mellem et al. |
| 2021/0383924 | A1 | 12/2021 | Rajan et al. |

FOREIGN PATENT DOCUMENTS

| | | |
|---|---|---|
| JP | 2015230199 A | 12/2015 |
| WO | 2016012864 A2 | 1/2016 |

OTHER PUBLICATIONS

Patel, Manesh R., et al. "Cardiovascular events in patients with Fabry disease: natural history data from the Fabry Registry." Journal of the American College of Cardiology 57.9 (2011): 1093-1099. (Year: 2011).*

Rozenfeld, Paula A. "Fabry disease: treatment and diagnosis." IUBMB life 61.11 (2009): 1043-1050. (Year: 2009).*

Weidemann, Frank, et al. "The variation of morphological and functional cardiac manifestation in Fabry disease: potential implications for the time course of the disease." European heart journal 26.12 (2005): 1221-1227. (Year: 2005).*

Conway, Robert. "The sphingolipidoses." Health care for people with intellectual and developmental disabilities across the lifespan. Springer, Cham, 2016. 659-682. (Year: 2016).*

Wang, Raymond Y., et al. "Lysosomal storage diseases: diagnostic confirmation and management of presymptomatic individuals." Genetics in Medicine 13.5 (2011): 457-484. (Year: 2011).*

Breunig, Frank, et al. "Fabry disease: diagnosis and treatment." Kidney International 63 (2003): S181-S185. (Year: 2003).*

Alam, Md Suhail, et al. "Genomic expression analyses reveal lysosomal, innate immunity proteins, as disease correlates in murine models of a lysosomal storage disorder." (2012): e48273. (Year: 2012).*

Aerts, Johannes MFG, et al. "Biomarkers in the diagnosis of lysosomal storage disorders: proteins, lipids, and inhibodies." Journal of inherited metabolic disease 34 (2011): 605-619. (Year: 2011).*

Beutler, E., et al. "Acid hydrolases in leukocytes and platelets of normal subjects and in patients with Gaucher's and Fabry's disease." The Journal of experimental medicine 143.4 (1976): 975-980. (Year: 1976).*

Cox, Timothy M. "Biomarkers in lysosomal storage diseases." Fabry disease: perspectives from 5 years of FOS (2006). (Year: 2006).*

Bobillo Lobato, Joaquin, Maria Jiménez Hidalgo, and Luis M. Jiménez Jiménez. "Biomarkers in lysosomal storage diseases." Diseases 4.4 (2016): 40. (Year: 2016).*

Oliveira, João Paulo, et al. "Splenomegaly, hypersplenism and peripheral blood cytopaenias in patients with classical Anderson-Fabry disease." Virchows Archiv 453 (2008): 291-300. (Year: 2008).*

Non-Final Office Action received for U.S. Appl. No. 15/913,663, dated Jul. 16, 2021, 18 pages.

Final Office Action received for U.S. Appl. No. 15/913,663, dated Jul. 21, 2020, 18 pages.

Notice of Allowance received for U.S. Appl. No. 15/913,663, dated Jan. 12, 2022, 8 pages.

Aerts et al., "Biomarkers in the diagnosis of lysosomal storage disorders: proteins, lipids, and inhibodies", Journal of Inherited Metabolic Disease, vol. 34: 605-619, Available online at: <https://doi.org/10.1007/s10545-011-9308-6>, Mar. 29, 2011, pp. 605-619.

Non-Final Office Action received for U.S. Appl. No. 15/913,663, dated Jan. 31, 2020, 16 pages.

Berk, P., et al., Studies of bilirubin kinetics in normal adults., J Clin Invest., 1969;48:2176-90.

Bhutani, V., et al., Predictive ability of a pre-discharge hour-specific serum bilirubin for subsequent significant hyperbilirubinenmia in healthy term and near-term newborns, Pediatrics 1999; 103:6-14.

Boo, N., et al., Prediction of severe hyperbilirubinaemia using the Bilicheck transcutaneous bilirubinometer. J Paediatr Child Health., 2007;43:297-302.

Dennery, P., et al., Neonatal blue-light phototherapy could increase the risk of dysplastic nevus development. Pediatrics. 2007;120:247-8.

Dennery, P., et al., Neonatal Hyperbilirubinemia., New England Journal of Medicine 2001; 334:581-90.

Dennery, P., Pharmacological interventions for the treatment of neonatal jaundice. Semin Neonatol. 2002;7:111-9.

Facchini, F., et al., Follow-up of neonatal jaundice in term and late premature newborns. J Pediatr (Rio J) 2004; 83:313-22.

Gartner, L, et al., Jaundice and breastfeeding Pediatr Clin North Am 2001; 48:389-99.

Gloria-Bottini, F., et al., Adenosine deaminase genetic polymorphism and the effect of smoking on neonatal bilirubinemia and developmental parameters. Early Hum Dev. Jun. 16, 2008.

Jangaard, K, et al., Outcomes in a population of healthy term and near-term infants with serum bilirubin levels >=19 mg/dL who were born in Nova Scotia, Canada, between 1994 and 2000. Pediatrics. 2008; 122:119-24.

Kaplan, M., et al., Evaluation of discharge management in the prediction of hyperbilirubinemia: the Jerusalem experience. J. Pediatr. 2007;150:412-7.

Keren, R., et al., A comparison of alternative risk-assessment strategies for predicting significant neonatal hyperbilirubinemia in term and near-term infants. Pediatrics. 2008;121:e170-9.

(56) References Cited

OTHER PUBLICATIONS

Kuzniewicz, M., et al., Risk factors for severe hyperbilirubinemia among infants with borderline bilirubin levels: a nested case-control study. J. Pediatr. 2005;153:234-40.

Moerschel, S., et al., A practical approach to neonatal jaundice. Am Fam Physician. 2008; 77:1255-62.

Ostrow, J., et al., Phototherapy for neonatal jaundice. N. Engl J Med. 2008;358(23):2534.

Zanardo. V., et al., Cytokines in human colostrum and neonatal jaundice. Pediatr Res. 2007;62:191-4.

Subcommittee on Hyperbilirubinemia, Management of Hyperbilirubinemia in the Newborn Infant 35 or More Weeks of Gestation, Pediatrics 2004; 114;297-316.

Gillespie, Robert S., et al., One size does not fit all: Interpreting Laboratory Data in Pediatric Patients, AMIA 2003 Symposium Proceedings—p. 850.

Setia, Sabeena, et al., Neonatal Jaundice in Asian, White and Mixed-Race Infants, Arch Pediatr Adolesc Med., vol. 156, Mar. 2002.

Bjerre, J, et al., Surveillance of extreme hyperbilirubinaemia in Denmark: A method to identify the newborn infants. Acta Paediatr. 2008;97:1030-4.

Petrone, E, et al., Early hospital discharge of the healthy term neonate: the Italian perspective. Minerva Pediatr. 2008;60:273-6.

Shortland, D., et al., Understanding neonatal jaundice; U.K. practice and international profile. J R Soc Health. 2008;128:202-6.

Ivanciuc, O., Applications of Support Vector Machines in Chemistry, Reviews in Computational Chemistry, vol. 23., 2007, p. 291.

Huang et al. "Risk Factors for Sever Hyperbilirubinemia in Neonates", Pediatric Research (2004) vol. 56, No. 5. pp. 682-689.

Pre-interview First Office Action received for U.S. Appl. No. 16/151,217, dated Mar. 28, 2022, 5 pages.

Sharma et al., "Machine Learning Based Analytics of Micro-MRI Trabecular Bone Microarchitecture and Texture in Type 1 Gaucher Disease", Journal of Biomechanics 49.9, available online at: <https://pubmed.ncbi.nlm.nih.gov/27109052/>, Jun. 14, 2016, pp. 1961-1968.

\* cited by examiner

EXAMPLE APPLICATION USER INTERFACE

| Patient aged between 6 and 60 years… | enter |
|---|---|
| Acroparesthesia? (Y/N) [ICD-9: 443.89,729.2, ICD-10: I73.8,M79.2,R20.2] | Y |
| Three or more of the listed comorbid conditions*? (Y/N) | Y |
| Urine protein > 100 mg/dL -or- "2+" or greater on UA dipstick/teststrip | Y |
| eGFR < 90 mL/min/1.73m²? (Y/N) | Y |
| RBC sedimentation rate > 10 mm/hr? (Y/N) | N |
| INR > 1.1 -and- not treated with warfarin? (Y/N) | N |
| PLT < 100K/uL? (Y/N) | Y |
| MPV > 10 fL? (Y/N) | N |
| RDW > 15.0 um? (Y/N) | Y |
| Monocytes,percent > 10%? (Y/N) | Y |
| Monocytes, absolute count > 1.0K/uL? (Y/N) | Y |

{ 310 }

| evaluate | results |
|---|---|
| data complete? | Yes |
| Likelihood of findings meriting GLA, GB3, and other testing.... | Moderate |

320 —

330 ⟶ [ 27% ]   332 ⟶ [ 10% ] to 336 ⟶ [ 54% ]

**\* Comorbid conditions**

| | ICD-9 | | ICD-10 | |
|---|---|---|---|---|
| Splenomegaly | 789.2 | | R16.1 | |
| Hypohidrosis -or- Anhidrosis | 705.0 | | L74.4 | |
| Heat intolerance -or- Hyperhidrosis | 780.8x | | R61.xx | |
| Fever, recurrent | 780.60 | | R50.9 | |
| Angiokeratoma | 216.9 | | D23.9 | |
| Cornea verticillata -or- Vortex keratopathy | 371.15 | 371.5x | H18.03x | H18.5xx |
| Vertigo | 780.4 | | R42 | |
| Headache | 784.0 | 339.xx | G44.xxx | R51 |
| Abdominal pain | 789.xx | | R10.xxx | |
| Diarrhea, chronic | 787.91 | | R19.7 | |
| Constipation, chronic | 564.0x | | K59.0x | |
| Early satiety -or- Anorexia | 780.94 | 783.0x | R68.81 | R63.0x |
| Tinnitus | 388.3x | | H93.1x | |
| Left ventricular hypertrophy | 429.3 | | I51.7 | |
| Hypertrophic cardiomyopathy | 425.1x | | I42.2 | |
| Prolonged QRS interval > 100 msec -or- Shortened PR interval < 130 msec -or- Low voltage on ECG | 426.7 | 426.81 | I45.6 | |

```
###########################################################################

#  Bayesian logistic regression model for small ICD-10 Fabry dataset

##################################################################### library(mcmc)

fab <- read.csv(file="c:/0_cerdsm/0__math_models/genzyme/fabry/dsm_fab10.csv", header=TRUE,
       colClasses=c("character",rep("integer",11),"numeric","factor"))
# pat,acro,comor,upro,egfr,sed,inr,plt,mpv,rdw,monop,monoa,score,fabry
fab <- fab[,-1]

# conventional logistic regression does not converge for so small and near-singular a dataset
# fit <- glm(fabry ~ ., data=fab, family=binomial(link=logit), epsilon=1e-4, maxit=100)
out <- glm(fabry ~ score, data=fab, family=binomial(), x=TRUE)

x <- out$x
y <- out$y
lupost <- function(beta, x, y) {
  eta <- as.numeric(x %*% beta)
  logp <- ifelse(eta < 0, eta - log1p(exp(eta)), - log1p(exp(- eta)))
  logq <- ifelse(eta < 0, - log1p(exp(eta)), - eta - log1p(exp(- eta)))
  logl <- sum(logp[y == 1]) + sum(logq[y == 0])
  return(logl - sum(beta^2) / 8)
} set.seed(42)
beta.init <- as.numeric(coefficients(out))
out <- metrop(lupost, beta.init, 1e3, x=x, y=y)
out <- metrop(out, scale=1.1, x=x, y=y)
out$accept
out <- metrop(out, nbatch=1e4, x=x, y=y)
out$accept str(out)
List of 13
# $ accept   : num 0.203
# $ batch    : num [1:10000, 1:2] -86.2 -86.2 -86.2 -86.2 -86.2 ...
# $ initial  : num [1:2] -86.4 26.2
# $ final    : num [1:2] -5.02 2.22

# compare              -5.11 0.89
```

*FIG. 5*

```
library(pROC)

ds4 <- read.csv(file="c:/0_cerdsm/IP/orphan_fabry/roc.csv")
roc1 <- roc(ds4[,1] ~ ds4[,2], percent=TRUE,
# arguments for auc
# partial.auc=c(100, 90), partial.auc.correct=TRUE,
#  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE)
```

*FIG. 6*

PREDICTING SPHINGOLIPIDOSES (FABRY'S DISEASE) AND DECISION SUPPORT

CROSS-REFERENCE TO RELATED APPLICATIONS

This application claims the benefit of U.S. Provisional Application No. 62/466,367; entitled "Predicting Sphingolipidoses (Fabry's Disease) and Decision Support," filed Mar. 3, 2017, which is expressly incorporated by reference in its entirety.

BACKGROUND

Lysosomal storage disorders are relatively rare inherited conditions involving enzyme deficiencies that can impair the functioning of many body organ systems by the accumulation of abnormal amounts of molecules in the lysosome organelles of the body's cells, usually producing severe disability and shortened life-expectancy. Effective treatments are available for some such disorders and may involve enzyme replacement therapy (ERT) involving ongoing periodic infusions of a synthetic recombinant version of the enzyme that is deficient, or stem cell transplantation, or other treatment modalities. Patients who have certain inherited lysosomal storage disorders, such as sphingolipidoses, have widely varied clinical courses and presentations. Symptoms are typically first experienced in early childhood and can be misinterpreted by physicians and other clinicians. Signs and symptoms of the disease usually increase in number and severity as an individual ages. Variations in the presenting signs and symptoms are so diverse as to pose significant diagnostic challenges for most clinicians. The comparative rarity of sphingolipidoses, such as Fabry's Disease, means that most clinicians might never encounter a single patient having such a disorder in their entire clinical career. As a result, many patients having such conditions may go years undiagnosed or, alternatively, are mis-diagnosed and are treated for many years on the basis of an incorrect diagnosis. Such erroneous misdiagnosis-based treatments (or non-treatments) are ineffective or even unsafe and impair the health of the patient or lead to needless progression of the disease or irreversible loss of body function.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

A diagnostic and decision support technology is provided for determining the presence, identity, and/or severity of an inherited lysosomal storage disorder. In particular, a mechanism is provided to detect and classify a lysosomal storage disorder in a human patient, which utilizes a logistic regression classifier determined based on a multi-variable-composite-biomarker comprising a specific set of physiological variables of the patient. This multi-variable statistical predictive biomarker approach may be employed for identifying persons whose attributes are consistent with features of sphingolipidoses, such as Fabry's Disease.

In embodiments, a multi-variable logistic regression statistical model capable of calculating a probability of a sphingolipidosis is generated. Using an input data set for a patient and the multi-variable logistic regression statistical model, a predicted probability of a sphingolipidosis is determined and presented to a clinician to guide decision-making regarding additional diagnostic or prognostic evaluation. Moreover, some embodiments further comprise technologies for scoring or ascertaining the severity of a previously-diagnosed sphingolipidosis condition in human patients, such as Fabry's disease, to assist in optimizing the medical treatment of individual patients and as a biomarker to follow the efficacy of treatment in animal models and in patients.

Based on this determined result (which may include one or more of a prediction, scoring, and/or severity), one or more actions may be carried out automatically or may be recommended, such as, without limitation, generating notifications such as electronic messages or alarms, based on said probability or score which may be emitted or otherwise provided to the caregiver and/or to the patient, advising them of the probability of an inherited sphingolipidosis meriting further diagnostic testing. In some embodiments, recommendations for specialist caregivers may be generated (or appointments may be automatically generated) and/or one or more EHR transactions may be automatically triggered by the determined result or score so as to initiate said diagnostic testing procedures. Some embodiments integrate with other decision support tools and related tools, such as Cerner Millennium orders, Discern Expert CDS, iView, or similar applications.

BRIEF DESCRIPTION OF THE DRAWINGS

The present technology is described in detail below with reference to the attached drawing figures, wherein:

FIG. 3 depicts an example graphical user interface of a multivariable predictive model component of a decision-support tool for predicting sphingolipidoses in a human patient, in accordance with an embodiment of the disclosure;

FIG. 5 illustratively provides an example embodiment of a computer program routine for predicting sphingolipidoses in accordance with an embodiment of this disclosure and further described in connection to FIGS. 2A and 2B; and FIG. 6 illustratively provides an example embodiment of a computer program routine for evaluating performance of an example embodiment reduced to practice and generating the ROC of FIG. 4A.

DETAILED DESCRIPTION

Figure 1A:
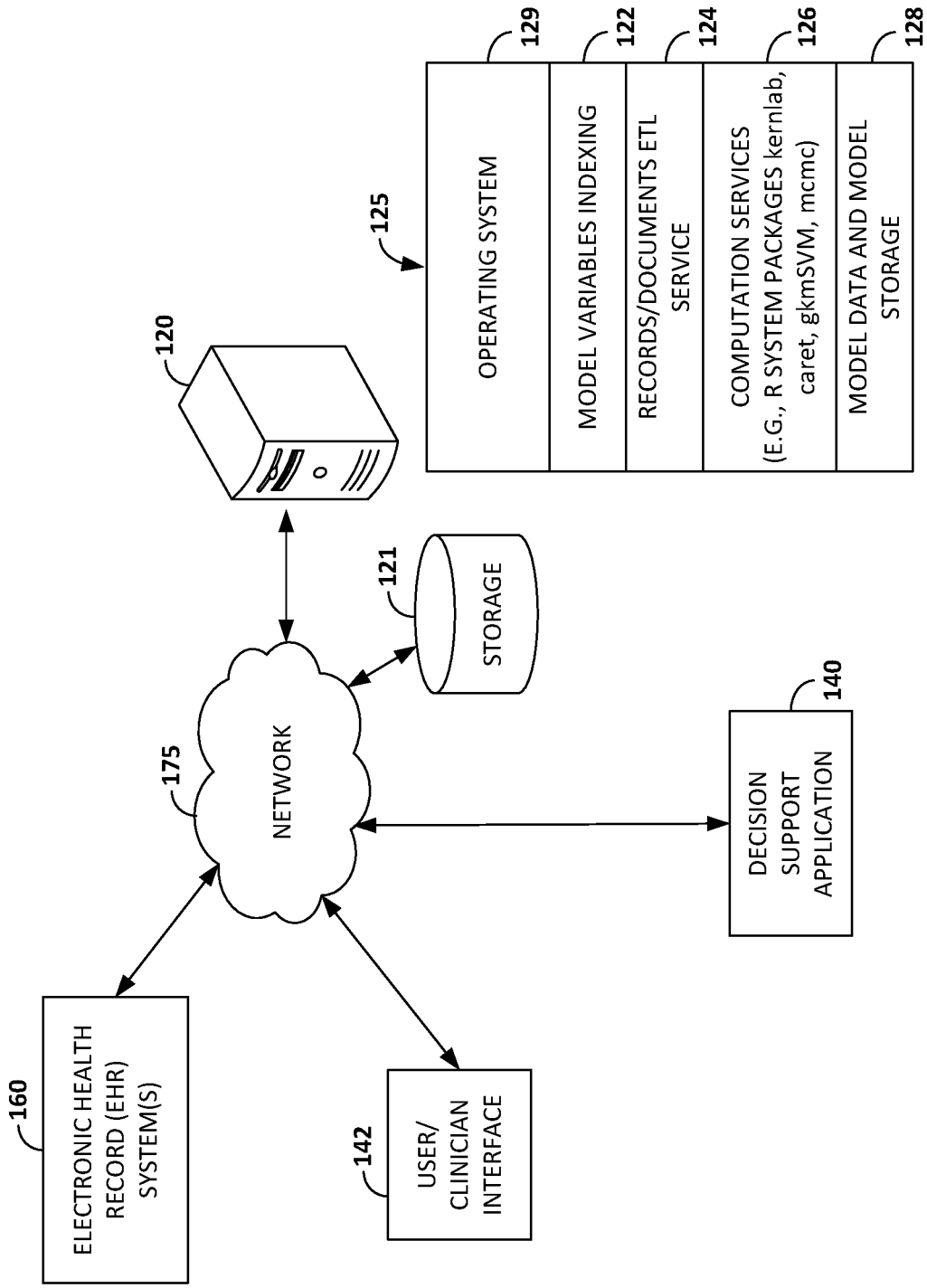
FIGS. 1A and 1B depict aspects of an illustrative architecture suitable for practicing an embodiment of the disclosure.

The subject matter of the present technology is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our disclosure may be embodied as, among other things: a method, system, or set of instructions embodied on one or more computer readable media. Accordingly, the embodiments may take the form of a hardware embodiment, a software embodiment, or an embodiment combining software and hardware. In one embodiment, the disclosure takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or non-transitory storage devices. These technologies can store data momentarily, temporarily, or permanently.

Aspects of the technology described herein may be utilized for a screening procedure and multi-variable logistic regression based biomarker, which determines a numerical probability of a sphingolipidosis condition, such as Fabry's Disease. Such technology is particularly valuable for patients in whom other diagnostic and prognostic means tend to yield excessive false-negative results. In particular, we determined that hypocoagulable abnormalities of the extrinsic coagulation cascade (as measured by prothrombin time or International Normalized Ratio INR, in the absence of treatment with warfarin or other anticoagulants) and a rightward shift in the statistical distribution of the blood platelets' volume are strongly statistically associated with a diagnosis of Fabry's disease. We have also determined that relative and absolute monocytosis and an increase in the red blood cell size distribution width (RDW) are associated with patients having sphingolipidoses or Fabry's disease. Utilizing our findings, which have not previously been reported in the known research literature, we developed a multi-variable composite biomarker pattern and predictive model, which we integrated into a decision-support system. In some embodiments, a decision support tool is provided, which may be a component in an electronic health records (EHR) system for detecting presence, identity, and/or severity of a lysosomal storage disorder in patients, for notifying caregivers, and/or generating a recommendation or automatically performing additional actions such as scheduling diagnostic testing, treatments, modification to care plans, or other intervening actions. For example, cone embodiment comprises generating a notification indicating a patient's probability or severity of a lysosomal storage disorder.

According to one embodiment, as will be further described herein, systems and computerized methods are provided for determining the presence, identity, and/or severity of a disease or condition in an individual, where the disease or condition is associated with a lysosomal storage disorder such as abnormal glycan biosynthesis, degradation, or accumulation. In some embodiments, these systems or methods are incorporated into a decision support tool used for screening, monitoring, and/or treating a patient. The decision support tool may utilize a multi-variable composite biomarker pattern and predictive model. In one embodiment, the biomarker patterns comprise a set or pattern of conditions or clinical events associated with a particular patient, which operate as independent variables in the model, and which may include: attribution of acroparesthesia; attribution of a plurality (e.g., three or more) specific comorbid conditions, which may be represented as a composite variable; proteinuria; reduced glomerular filtration rate or creatinine clearance; elevated erythrocyte sedimentation rate; increased prothrombin time or International Normalized Ratio (INR); decreased platelet count; increased mean platelet volume; increased red blood cell distribution width (RDW); and/or absolutely and/or relatively increased monocytes in a WBC differential count. In one embodiment, the specific comorbid conditions include: splenomegaly, hypohidrosis or anhidrosis, hyperhidrosis, recurrent fevers, angiokeratoma, cornea *verticillata*, vertigo, headach, abdominal pain, diarrhea, constipation, early satiety or anorexia, tinnitus, left ventricular hypertrophy, hypertrophic cardiomyopathy, and/or prolonged QRS interval or shortened PR interval or low voltage on electrocardiogram as a composite variable.

Based on the multi-variable composite biomarker pattern, a predictive model and model coefficients are instantiated. A patient is identified and EHR information for the patient is accessed. The EHR information may include demographic, diagnostic, and laboratory information about the patient. Inputs for variable values corresponding to the biomarker pattern are received from the patient's EHR, and a probability is determined from the model. In some embodiments, the determined probability may be considered a score denoting the likelihood of the patient's having a sphingolipidosis condition.

Next the determined probability or score is compared to one or more thresholds for lysosomal storage disorder diagnostics. In some embodiments, based on the comparison, one or more risk levels are determined associated with the probability or severity of a lysosomal storage disorder in the patient. Based on the comparison to the one or more thresholds, if the threshold(s) are not exceeded, then routine care for the patient may be carried out, as clinically indicated. But where the one or more thresholds are satisfied, then one or more intervening actions may be invoked. The one or more actions may be based on the determined probability or score satisfying the threshold(s) or the specific value of the determined probability or score. In some embodiments, an explanatory analysis may be prepared to accompany the model, for the significant values and deviations. Further, in some embodiments, an application and graphical user interface are provided for displaying a probability result or score denoting the likelihood of the patient's having a sphingolipidosis condition.

As described above, due to the rarity of sphingolipidoses, many clinicians might never encounter a single patient having such a disorder in their entire clinical career, which leads to many patients having such conditions may go years undiagnosed or may be mis-diagnosed. Such erroneous misdiagnosis-based treatments (or non-treatments) are ineffective or even unsafe and impair the health of the patient or lead to needless progression of the disease or irreversible loss of body function. In particular, conventional approaches to detecting this condition entails measuring lysosomal enzyme levels or other specific gene products, or levels of sphingolipid or glycosaminoglycan compounds that result from the presence of or deficiencies in the enzyme activity of enzymes related to sphingolipid metabolism (including, e.g., oligosaccharides, monosaccharides, sulfate, phosphate, sialic acid, acetate, or the like). Yet other conventional approaches entail genotyping or sequencing or other genomics or proteomics testing. Some of these methodologies involve invasive means, such as tissue biopsy or other surgical procedures, and many of these conventional approaches are not widely available.

Moreover, these conventional approaches involve expensive, time-consuming tests and are therefore neither practical or suitable to utilize for the purposes of screening large numbers of prospective patients for possible lysosomal storage disorders. In contrast, embodiments of technology described herein solve these problems by providing a convenient, rapid, and inexpensive screening system and method that relies upon information that may already have been determined in the course of providing routine care and diagnostic testing or that, at most, requires limited additional measurements that are widely available in most health facilities. In some embodiments, based on our findings (discussed previously), the present technology can utilize information determined from routine diagnostic testing provided at various medical facilities and stored electronically. Thus, in some embodiments, the present technology provides for using information derived from multiple patients, over time, and at different healthcare facilities through EHR systems. Therefore, computer functionality is improved and advanced over conventional technologies, as the computer may now make predictions for a patient having a potential sphingolipidosis condition, which have less false-negative results than conventional methods of trying to diagnostically test each individual patient, which may or may not be initially performed on a patient based on the treating clinician's experience with such rare conditions. In some embodiments of the technology described herein, if the probability or risk of a sphingolipidosis condition that is predicted by an embodiment of this technology exceeds a threshold, then electronic communication with the attending clinician may be generated and one or more EHR transactions may be initiated, such that diagnostic interventions (including more expensive, or time-consuming testing) capable of ruling-in or ruling-out said sphingolipidosis condition are undertaken. Accordingly, embodiments of this technology may be utilized as a screening means to afford timely, accurate, and cost-effective definitive diagnosis in a substantially larger cohort of persons at-risk than has heretofore been practical.

Accordingly, in an example embodiment, a computerized method of initiating an intervention action for sphingolipidosis is provided. The method comprises: based on a set of physiological variables associated with an individual that is received as input, determining a multi-variable biomarker based on a set of physiological variables in the input data, the multi-variable biomarker comprising a plurality of: attribution of acroparesthesia, attribution of a plurality of comorbid conditions, proteinuria, reduced glomerular filtration rate or creatinine clearance, elevated erythrocyte sedimentation rate, increased prothrombin time or International Normalized Ratio (INR), decreased platelet count, increased mean platelet volume, increased red blood cell distribution width (RDW), and absolutely or relatively increased monocytes in a WBC differential count; receiving a multi-variable logistic regression statistical model generated to determine a probability of clinically significant sphingolipidosis; determining the probability of clinically significant sphingolipidosis for the individual based on the multi-variable biomarker and the multi-variable logistic regression statistical model, wherein the multi-variable biomarker is used by the multi-variable logistic regression statistical model; and based on the probability of clinically significant sphingolipidosis for the individual, initiating the intervention action, the intervention action comprising one or more of modifying treatment of the individual, ordering additional diagnostics for the individual, scheduling treatment or diagnostics for the individual, and issuing a notification to a caregiver.

In another example embodiment, one or more computer-readable storage devices storing computer-useable instructions that, when used by one or more computing devices, cause the one or more computing devices to perform a method of initiating an intervention action for sphingolipidosis. The method comprises: based on a set of physiological variables associated with an individual that is received as input, determining a multi-variable biomarker, the multi-variable biomarker comprising a plurality of: attribution of acroparesthesia, attribution of a plurality of comorbid conditions, proteinuria, reduced glomerular filtration rate or creatinine clearance, elevated erythrocyte sedimentation rate, increased prothrombin time or International Normalized Ratio (INR), decreased platelet count, increased mean platelet volume, increased red blood cell distribution width (RDW), and absolutely or relatively increased monocytes in a WBC differential count; receiving a multi-variable logistic regression statistical model generated to determine a probability of clinically significant sphingolipidosis; determining the probability of clinically significant sphingolipidosis for the individual based on the multi-variable biomarker and the multi-variable logistic regression statistical model, wherein the multi-variable biomarker is used by the multi-variable logistic regression statistical model; and based on the probability of clinically significant sphingolipidosis for the individual, initiating the intervention action, the intervention action comprising one or more of modifying treatment of the individual, ordering additional diagnostics for the individual, scheduling treatment or diagnostics for the individual, and issuing a notification to a caregiver.

In yet another example embodiment, one or more computer-readable storage devices storing computer-useable instructions that, when used by one or more computing devices, cause the one or more computing devices to perform a method of initiating an intervention action for sphingolipidosis. The method comprises: identifying an EMR associated with an individual; receiving a multi-variable logistic regression statistical model generated to determine a probability of clinically significant sphingolipidosis; receiving input data from the EMR associated with the individual; determining a multi-variable biomarker based on a set of physiological variables in the received input data, the multi-variable biomarker comprising a plurality of: attribution of acroparesthesia, attribution of a plurality of comorbid conditions, proteinuria, reduced glomerular filtration rate or creatinine clearance, elevated erythrocyte sedimentation rate, increased prothrombin time or International Normalized Ratio (INR), decreased platelet count, increased mean platelet volume, increased red blood cell distribution width (RDW), and absolutely or relatively increased monocytes in a WBC differential count; determining the probability of clinically significant sphingolipidosis for the individual based on the multi-variable biomarker and the multi-variable logistic regression statistical model, wherein the multi-variable biomarker is used by the multi-variable logistic regression statistical model; and based on the probability of clinically significant sphingolipidosis for the individual, initiating the intervention action, the intervention action comprising one or more of modifying treatment of the individual, ordering additional diagnostics for the individual, scheduling treatment or diagnostics for the individual, and issuing a notification to a caregiver.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the present disclosure. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example system 200, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the technologies described herein, sequence itemset mining is performed using data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, bedside, or in-home patient monitors or sensors, for example.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system 160 directly. An embodiment of manager application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients having a lysosomal storage disorder. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; variables measurements, timeseries, and predictions (including plotting or displaying the determined outcome and/or issuing an alert) described herein; or other health-related information, and facilitates the display of results, recommendations, or orders, for example. In an embodiment, application 140 also facilitates receiving orders, staffing scheduling, or queries from a user, based on the results of monitoring and/or forecasted outputs, which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical or psychiatric caregiver or the like) to a score or prediction determined according to the technologies described herein, including information indicating a likelihood that a patient has a lysosomal disorder, the severity of the disorder, and/or additional classification of the disorder, such as the likelihood of a specific condition (e.g., Fabry's disease). One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined probability or score, recommendations, scheduling orders, providing instructions, or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for providing diagnostic services or evaluation of the performance of various embodiments. One example embodiment of a user/clinician interface 142 and decision support application 140, which is actually reduced to practice is illustratively provided in FIG. 3, which is further described below.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing service 122 and records/documents ETL service 124 provide services that facilitate retrieving patient physiological variables, which may include frequent item sets, extracting database records, and cleaning the values of variables in records. For example, services 122 and/or 124 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 may perform statistical or computing operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as packages kernlab, for kernel-based machine learning classification, regression, clustering, and dimensionality reduction methods; caret, for training classification and regression models; gkmSVM, for implementing a Gapped-Kmer Support Vector Machine; and mcmc, for Markov Chain Monte Carlo operations. Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 5 and 6. Computation services 126 also may include services or routines for utilizing one or more prediction, forecasting, or diagnostic models, such as the models described in connection to FIGS. 2A and 2B and the example computer program routines illustratively provided in FIG. 5. In some embodiments, computation services 126 use EHR system(s) 160, model data and model storage services 128, and/or other components of example operating environment 100, and may also include services to facilitate receiving and/or pre-processing physiological data. Model data and model storage services 128 may be utilized to perform services for facilitating storage, retrieval, and implementation of the models described herein and of the data used in the models.

Some embodiments of stack 125 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the present disclosure also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
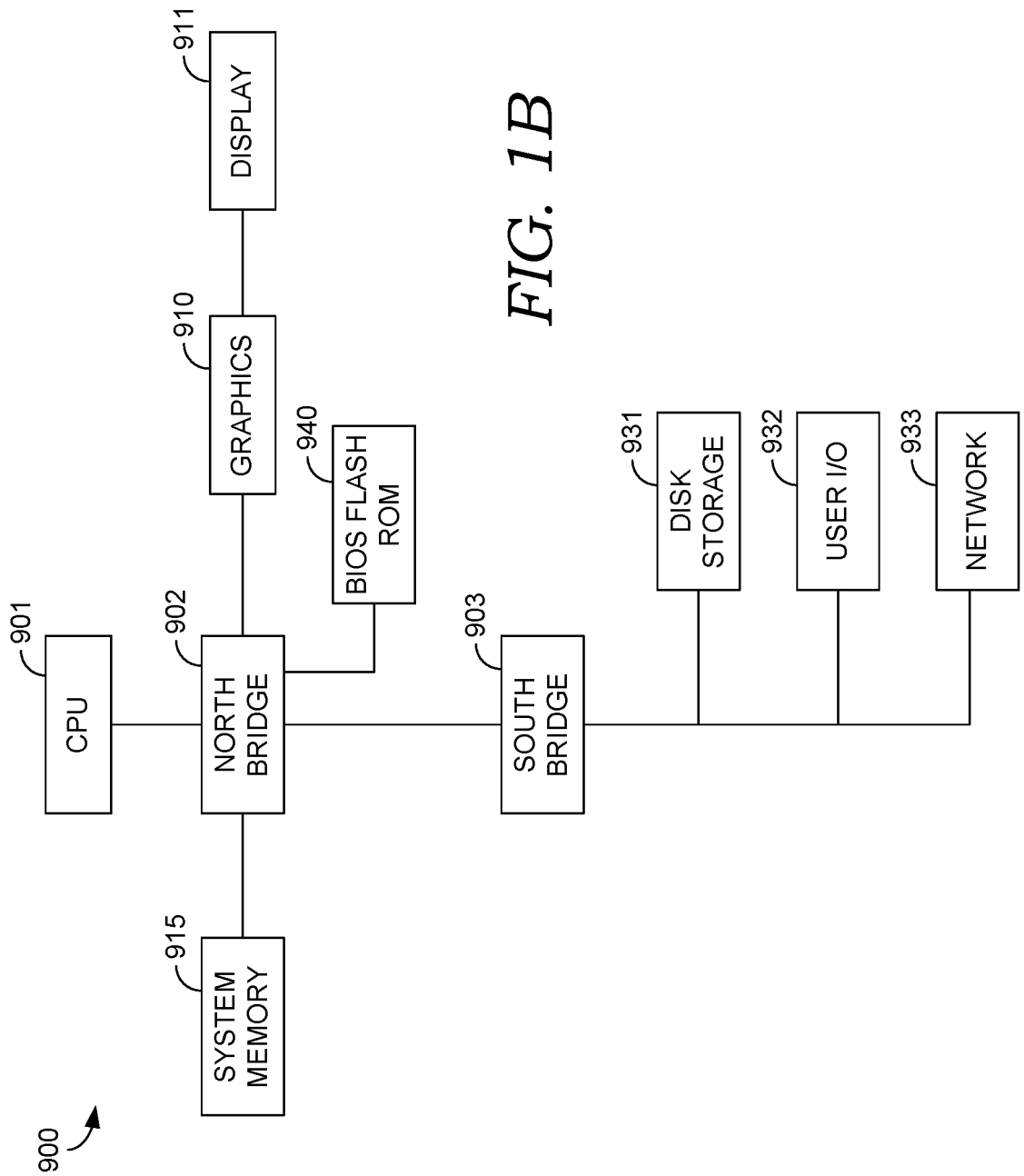

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a stylus or touch-stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In some embodiments, operating environment 100 (or the components of example operating environment 100) include an interface module (or equivalent functionality) for receiving incoming medical data from EHR system(s) 160, a transformation module for transforming the values of input variables referenced in the logistic regression model into intermediate values through dichotomization about a numeric threshold or logical conjunction or sum to totalize individual diagnosis attributions into a composite variable, and a combination module for determining the result of the probability calculation.

Figure 2A:
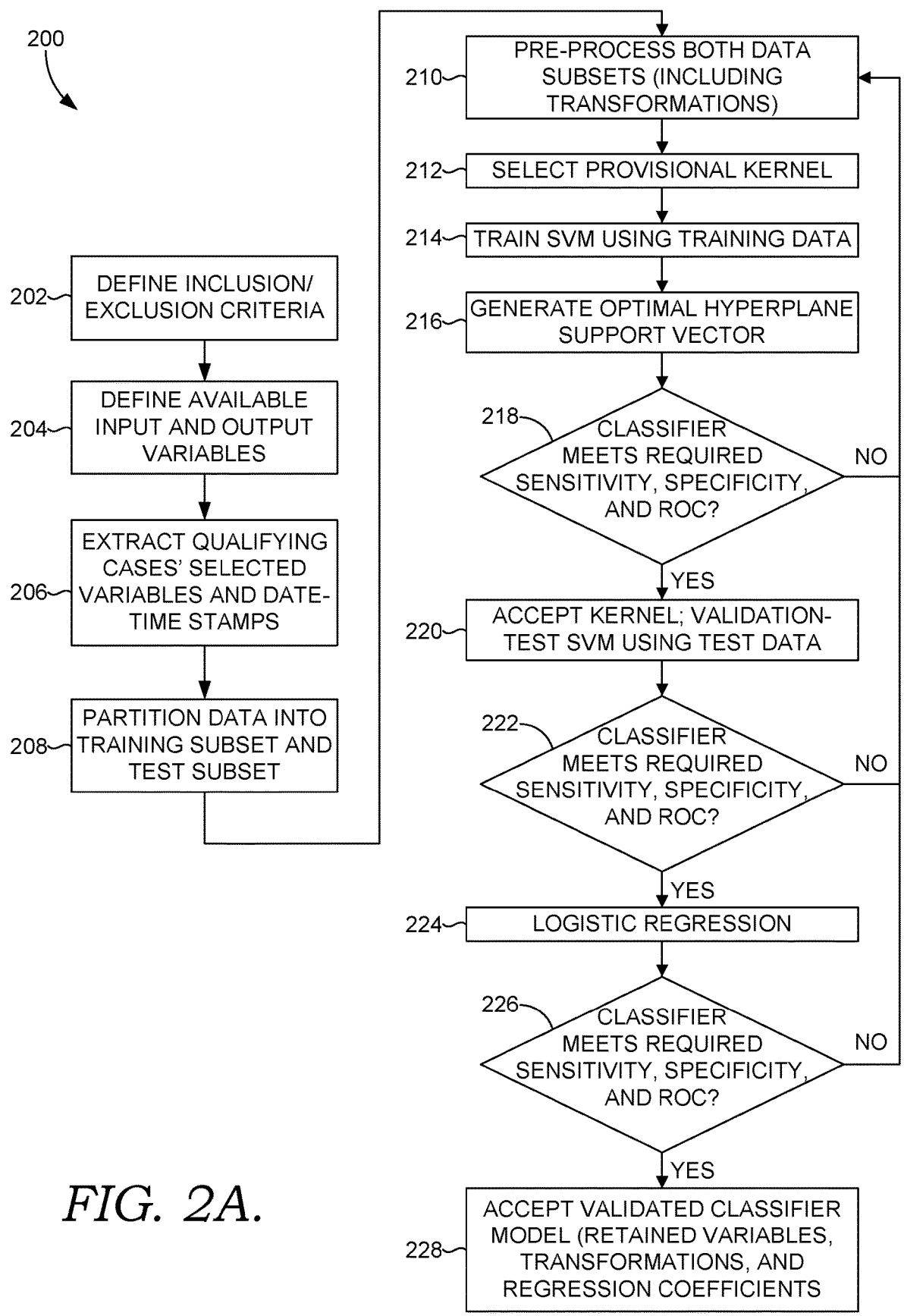
FIG. 2A depicts a flow diagram showing a method for producing and validating a statistical model for accurately predicting a lysosomal storage disorder in accordance with an embodiment of the disclosure.

Turning now to FIG. 2A, a flow diagram is provided that illustrates a method 200 for producing and validating a statistical model for accurately predicting sphingolipidoses in accordance with an embodiment of the technologies described herein. Initially, inclusion-exclusion criteria is defined, as shown at step (or block) 202, as well as problem specification in terms of available input and output variables, at step 204. Thereafter, as shown at step 206, training data is received. Training data comprises a set of data points having known characteristics. This data may come from research facilities, academic institutions, commercial entities, and/or other public or confidential sources. In the case of the present example embodiment, the data came from an anonymized data warehouse of U.S. hospitals' electronic medical record (EMR) data. The collection of training data may be accomplished manually or by way of an automated process, such as known electronic data transfer methods. Accordingly, an example embodiment of the learning machine for use in conjunction with the present disclosure may be implemented in a networked computer environment.

With reference again to step 202, it is known to those practiced in the art that to construct an effective classifier, appropriate inclusion-exclusion criteria may first be defined in sufficient detail that the cases acquired for the purpose of classifier design accurately represent the population to which the classifier is intended to be applied. By way of example only and not limitation, the inclusion criteria include patients having sphingolipidoses. Some criteria for case inclusion in classifier development pertain to the dependent variables or 'outcomes' that are the object of the classification.

With reference again to step 204, for the cohort meeting the applicable inclusion-exclusion criteria, database retrieval of extant EMRs is performed. This serves to define the available input and output clinical and laboratory variables and characterize the descriptive statistics of each variable and assess the degree of "missingness" of information for each variable. In one embodiment, variables whose values are missing at a greater than 20% rate are excluded from subsequent consideration in classifier construction and development. It should be understood that, although database retrieval of EMRs is described, any type of patient medical or health record may be utilized within the various embodiments of the present disclosure (in the context of method 200 or in other contexts of embodiments described herein).

Next, at step 206, information for the qualifying cases for each of the selected variables is extracted from the EMR or other data source, including the date-time stamp for each item. As shown at step 208, the retrieved cases and case information are partitioned into two subsets—a first subset that is to be utilized for classifier construction and training (training data subset), and a second subset that is to be used for classifier validation testing (test data subset). Any of a variety of partitioning methods can be employed such as are well-known to statisticians practiced in the art. Randomized 'bootstrap' sampling without replacement, for example, may be used to insure that the subsets that are generated are not biased with regard to time, source institutions, or other factors. In some embodiments, the partitioning is made into two subsets of equal size (50%-50%). However, there is no requirement that this be the case. The subsets can be of different sizes. In some embodiments, the sample size of each subset is sufficient to achieve a desired 80% or greater statistical power for classification of the cases.

As shown at step 210, statistical pre-processing may be performed, including calculation of mean, median, standard deviation, skewness, and kurtosis for each of the numerical variables and frequency tables for each of the categorical variables. In instances where the statistical distribution of a numerical variable is markedly skewed, then logarithmic or power-law or other transformation of that variable is performed by methods that are well-known to statisticians, so as to produce a distribution for the transformed variable that is symmetrical and more nearly Gaussian in shape than that of the raw variable. The collected training data is optionally pre-processed in order to allow the learning machine to be applied most advantageously toward extraction of the knowledge inherent in the training data. During this preprocessing stage, a variety of different transformations can be performed on the data to enhance its usefulness. Such transformations, examples of which include addition of expert information, spline conversion, logarithmic or power-law transformations, etc., will be readily apparent to those of skill in the art. However, the preprocessing of interest in an embodiment of the present disclosure is the reduction of dimensionality by way of feature selection.

The resulting dataset is processed with a Support Vector Machine (SVM) algorithm and a provisional kernel is selected, as shown at step 212. Some embodiments of method 200 (and method 201 in FIG. 2B) utilize computation services 126 (FIG. 1), including R System package gkmSVM. AN SVM is a specific type of learning machine that implements a specialized algorithm for providing generalization when estimating a multi-dimensional function from a limited collection of data. The training data subset is used to condition the SVM kernel coefficients and generate a support vector (or hyperplane of the variables) at step 216 that optimally distinguishes the cases according to the dependent variable, which in one embodiment is the outcome of a patient being diagnosed with sphingolipidoses. AN SVM may be used in estimating classification functions (e.g., pattern-recognition problems) and real-valued functions (e.g., function approximation problems and regression estimation problems). Those skilled in the art should appreciate that SVMs are capable of processing input data having extremely large dimensionality. However, in some embodiments, pre-processing includes the use of feature selection methods to reduce the dimensionality of feature space.

As shown at step 214, the SVM is trained using the pre-processed data from the training data subset. Accordingly, the SVM is trained by adjusting its operating parameters until a desirable training output is achieved. The determination of whether a training output is desirable may be accomplished by comparing the training output to the known characteristics of the training data. A learning machine is considered to be trained when its training output is within a predetermined error threshold from the known characteristics of the training data.

As is known in the art, different kernels will cause an SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge, such as the relation of various clinical and laboratory variables to liver function relevant to bilirubin metabolism, transport, and excretion. As is known in the art, example kernels include polynomial kernels, radial basis function (RBF) classifier kernels, linear kernels, etc. In an alternate embodiment, a customized kernel may be created that is specific to a particular problem or type of data set. The quality of the outputs for each simultaneously trained and tested SVM may be compared using a variety of selectable or weighted metrics to determine whether the kernel chosen performs sufficiently well or whether an alternative kernel achieves superior performance.

At step 218, the resulting classification table is examined by available receiver-operating characteristic (ROC) statistical software, to assess whether the classifier generated by the SVM meets the design requirements established for the predictive model. According to one embodiment, a minimum ROC area-under-the-curve (C-statistic) of 0.80 is required before a model is an acceptable candidate for consideration for logistic regression and subsequent processing and validation. In the event that ROC is lower than the acceptable minimum, then additional iterations of variables selection, pre-processing, kernel generation, and SVM support vector generation are performed (steps 210-218). Alternatively, if ROC is determined to be acceptable at step 218, then the kernel and support vector are accepted and the model is validation-tested, as shown at step 220, using the test data subset that was previously prepared and reserved at step 208. One example ROC for an example embodiment actually constructed using a predictive model generated according to method 200 is illustratively shown in FIG. 4A.

Additionally, an example computer program routine for generating the ROC according to method 200 is illustratively provided in FIG. 6.

Figures 4A, 4B:
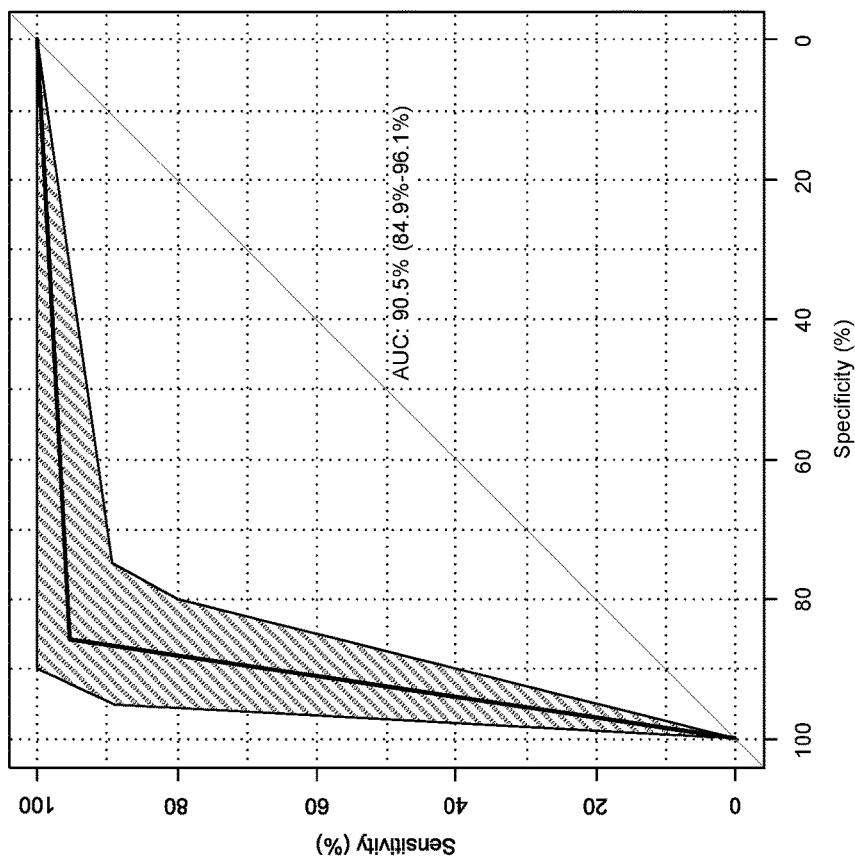
FIGS. 4A and 4B depict aspects of the statistical performance of an example embodiment for predicting sphingolipidoses actually reduced to practice, including a receiver operating characteristic (ROC) curve and statistical performance measures.

Based on the post-processed test output, it is determined at steps 222, 224, and 226 whether an optimal minimum was achieved by the SVM and logistic regression. Those skilled in the art should appreciate that an SVM is able to ascertain an output having a global minimum error. However, as mentioned above, output results of an SVM for a given data set will typically vary with kernel selection. Therefore, there are in fact multiple global minimums that may be ascertained by an SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by an SVM. Accordingly, at step 222, determining whether the optimal minimum has been ascertained may involve comparing the output of an SVM with a historical or predetermined value. One example of the statistical performance, which may be assessed in step 222 is shown in FIG. 4B, which includes statistical performance measurements for the example embodiment actually reduced to practice, described above.

If it is determined that the optimal minimum has not been achieved by the trained SVM, the method moves to step 210, and kernel selection is readjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method is repeated from step 212, where the pre-processed training data is input into the SVM for training purposes. When it is determined at step 222 that the optimal minimum has been achieved, test data is collected in manners similar to those described above. By definition, live data has not been previously evaluated so that the desired output characteristics that were known with respect to the training data and the test data are not known.

Additional test data is optionally collected in preparation for testing the trained SVM. Test data may be collected from one or more local and/or remote sources. In some embodiments, test data and training data may be collected from the same source(s) at the same time. Thus, test data and training data sets can be divided out of a common data set and stored in a local storage medium for use as different input data sets for a learning machine. Regardless of how the test data is collected, any test data used is pre-processed at step 210 in the same manner as was the training data. As should be apparent to those skilled in the art, a proper test of the learning machine may be accomplished by using testing data of the same format as the training data. Then, at step 220, the learning machine is tested using the pre-processed test data, if any. The test output of the learning machine is optionally post-processed in order to determine if the results are desirable. Again, the post processing step involves interpreting the test output into a meaningful form. The meaningful form may be one that is readily understood by a human or one that is compatible with another processor. Regardless, the test output may be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations (such as logit or probit equations).

After validation testing has confirmed a vector of variables and transformations that achieves acceptable sensitivity, specificity, and ROC performance, a logistic regression model is calculated, at step 224, utilizing the input variables and transformations that were developed and validated in the previous steps. The generation of the logistic regression model may be done using the training data subset or the entire original dataset or other partitions derived from it, depending on missing data for some variables or other pragmatic factors. Embodiments of method 200 do not depend upon any particular partitioning at this step. Indeed, the sample size available may often dictate what partitioning is possible, insofar as logistic regression does not tolerate missing data elements. If a decision is made to retain cases that contain missing data in the logistic regression step, then hot-deck or last-value-carry-forward, or other imputation methods may be used, such as are familiar to statisticians.

Finally, the statistical performance of the resulting logistic regression classifier, including its ROC c-statistic, is assessed and, if adequate to the intended purpose, accepted for implementation, as shown at steps 226 and 228. Accepted classifiers may be stored as predictive models utilizing model data and model storage services 128, described in FIG. 1. These predictive models then may be utilized, as described in method 201 (FIG. 2B) for determining presence, identity, and/or severity of a lysosomal storage disorder in a patient.

Utilizing method 200, a set of physiological variables were determined for independent model variables. In particular and in some embodiments, these model variables function as a multi-variable composite biomarker and include: attribution of acroparesthesia; attribution of a plurality (e.g., three or more) specific comorbid conditions, which may be represented as a composite variable; proteinuria; reduced glomerular filtration rate or creatinine clearance; elevated erythrocyte sedimentation rate; increased prothrombin time or International Normalized Ratio (INR); decreased platelet count; increased mean platelet volume; increased red blood cell distribution width (RDW); and/or absolutely and/or relatively increased monocytes in a WBC differential count. In one embodiment, the specific comorbid conditions include: splenomegaly, hypohidrosis or anhidrosis, hyperhidrosis, recurrent fevers, angiokeratoma, cornea *verticillata*, vertigo, headach, abdominal pain, diarrhea, constipation, early satiety or anorexia, tinnitus, left ventricular hypertrophy, hypertrophic cardiomyopathy, and/or prolonged QRS interval or shortened PR interval or low voltage on electrocardiogram as a composite variable.

Figure 2B:
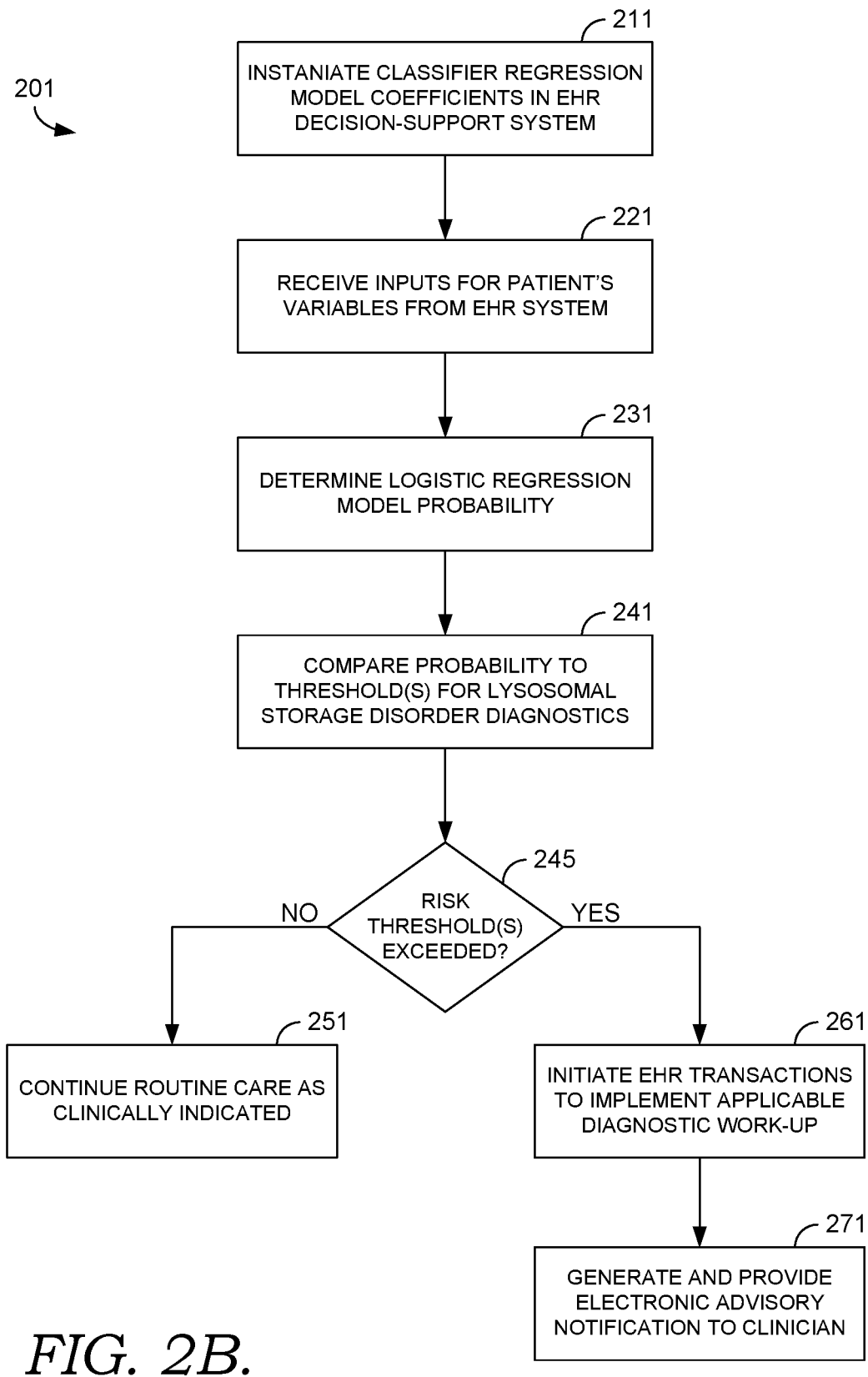
FIG. 2B depicts a flow diagram of an example method for determining presence, identity, and/or severity of a lysosomal storage disorder using a multi-variable logistic regression statistical model, in accordance with an embodiment of the disclosure.

Turning now to FIG. 2B, a flow diagram is provided illustrating a method 201 for determining presence, identity, and/or severity of a lysosomal storage disorder using a multi-variable logistic regression statistical model, which may be determined according to method 200 (FIG. 2A). At step 211, instantiate classifier regression model coefficients. Embodiments of step 211 initiate a predictive model having coefficients corresponding to independent model variables. In some embodiments of step 211, the prediction model comprises classifier regression model for classifying likelihood of a patient having a lysosomal storage disorder and may be determined according to method 200 (FIG. 2A). In some embodiments, the model is generated using a support vector machine, gradient boosting, or other machine-learning means to reduce the initial dimensionality of the statistical analysis. In some instances, the model (or computer-instructions for instantiating the model when called upon) may be incorporated into a decision-support tool for use by a caregiver, such as a health care professional. Some embodiments integrate with other decision support tools and related tools, such as Cerner Millennium® orders, Discern® Expert CDS, iView®, or similar applications.

At step 221, a patient is identified and EHR information for the patient is accessed. The EHR information may include demographic, diagnostic, and laboratory information about the patient. In particular, at step 221, inputs for variable values corresponding to the independent variables of the classifier model may be received from the patient's EHR. At step 231, a probability is determined. In some embodiments, the determined probability may be considered a score denoting the likelihood of the patient's having a sphingolipidosis condition. Some embodiments of steps 231 may be performed using computation services 126 (described in connection to FIG. 1A). In particular, aspects of method 201 may be carried out using the example computer program provided in FIG. 5.

At step 241, the determined probability or score is compared to one or more thresholds for lysosomal storage disorder diagnostics. In some embodiments, the threshold(s) may be predetermined, determined empirically, or based on information about the particular patient, caregiver, or other treatment context (e.g., the treatment venue, role of the caregiver, insurer, or other clinical conditions or events associated with the patient). In some embodiments, step 241 comprises correlating the magnitude of the composite biomarker with the presence, identity, and/or severity of the disease or condition by comparing the probability against a set of thresholds indicating a presence, identity, and/or severity of a disease or condition associated with the patient. For example, the disease or condition may include a lipidosis or sphingolipidosis including a lysosomal storage disease such as gangliosidosis or Fabry's Disease (e.g., alpha-galactosidase A deficiency). In some embodiments, based on the comparison in step 241, one or more risk levels are determined associated with the probability or severity of a lysosomal storage disorder in the patient.

At step 245, based on the comparison to the one or more thresholds, if the threshold(s) are not exceeded, then at step 251 routine care for the patient may be carried out, as clinically indicated. But where the one or more thresholds are satisfied, then method 201 proceeds to step 261 and one or more intervening actions may be invoked. In particular, at step 251, additional diagnostics (such as more expensive or time-consuming testing) may be performed on the patient. In addition or in the alternative, other intervening actions may be performed. These actions may be based on the determined probability or score satisfying the threshold(s) or the specific value of the determined probability or score. For example, such actions may comprise generating and providing an electronic notification at step 271 (such as a message or alert) to the patient or a caregiver regarding the determined presence, identity, and/or severity of the lysosomal storage disorder in the patient, for instance, a message advising a caregiver of the probability of an inherited sphingolipidosis meriting further diagnostic testing; generating and providing a specific recommendation regarding the treatment or care of the patient (including recommending diagnostics, courses or care, or additional screenings), and/or automatically performing additional actions such as scheduling diagnostic testing, treatments, modification to care plans, or other intervening actions. In one embodiment, an EHR transaction is initiated to implement applicable diagnostic work-up of additional testing procedures for the patient. In some embodiments, an explanatory analysis may be prepared to accompany the model, for significant values and deviations. Further, in some embodiments, the determined score, severity, specific-condition classifications, and/or any recommended actions may be provided via a graphical user interface such as the example user interface shown in FIG. 3.

EXAMPLE REDUCTION TO PRACTICE

Turning now to FIG. 3, an application graphical user interface 300 is illustratively provided for an example embodiment actually reduced to practice (described below). In some embodiments, Example application interface 300 may be embodied as user/clinician interface 142 and/or decision support application 140, described in connection to FIG. 1. Example application interface 300 may comprise a component of a decision-support tool for predicting sphingolipidoses in a human patient, based on a multivariable predictive model, such as a model determined according to method 200.

Example application interface 300 includes a set of model variables 310, which comprise independent model variables for the prediction model. The set of variables (or in some embodiments, a subset of these variables) may be utilized according to a process, such as method 201, to determine likelihood and/or severity of a condition and thus function as a multi-variable composite biomarker. In some embodiments, variables 310 comprise one or more physiological variables, which may be a raw physiological variable or comprises an interpretation of a raw physiological data about the patient, such as whether a patient has three or more comorbid conditions (such as those shown at item 340) or whether eGFR is less than 90 mL/min/1.73 m2. Accordingly, example application interface 300 may be used by a clinician for acquisition of the values of variables that contribute to the biomarker, and for display of the value of the determined biomarker.

In the example application interface 300, to determine likelihood and severity, each physiological variable corresponds to a coefficient as follows: Acroparesthesia: 1.26; three or more of the listed comorbid conditions: 1.02; urine protein >100 mg/dL-or-"2+" or greater on UA dipstick/teststrip: 0.88; eGFR <90 mL/min/1.73 m2: 0.71; RBC sedimentation rate >10 mm/hr: 0.63; INR >1.1-and-not treated with warfarin: 0.62; PLT <100K/µL: 0.46; MPV >10 fL: 0.43; RDW >15.0 µm: 0.42; Monocytes, percent >10-percent: 0.19; Monocytes, absolute count >1.0K/µL: 0.13. Where the physiological variable is not present (including where the interpretation criteria is not satisfied, such as, for instance, where eGFR is present but exceeds 90 mL/min/1.73 m2), then the coefficient is set to zero.

Example application interface 300 includes a prediction result 320 indicating the patient's likelihood or severity of having the particular condition and thus warranting further testing. In this example, based on the specific values of the model variables 310, the likelihood is determined as "moderate." Example application interface 300 also includes items 330, 332, and 336. At item 330, a likelihood score is shown (here "27%"). In one embodiment, the likelihood score may be determined using logistic regression as:

$$\frac{e^{(05.11+0.89[\text{sum of the model variable coefficients}])}}{1+e^{(05.11+0.89[\text{sum of the model variable coefficients}])}}$$

Items 332 and 336 comprise an example range corresponding to the likelihood shown at result 329. In this example, item 332 is determined as:

$$\frac{e^{(05.11+0.64[\text{sum of the model variable coefficients}])}}{1+e^{(05.11+0.64[\text{sum of the model variable coefficients}])}}$$

and item 336 is determined as:

$$\frac{e^{(05.11+1.14[\text{sum of the model variable coefficients}])}}{1+e^{(05.11+1.14[\text{sum of the model variable coefficients}])}}$$

Reduction to practice and testing was accomplished using a server cluster (computer system 120) running the Linux operating system (operating system 129), the open-source statistical software package R (software services 126), and the R packages kernlab, caret, and gkmSVM, which were utilized for dimensionality reduction by SVM and gradient boosting methodsm and in particular, using the example computer program routine illustratively depicted in FIG. 5. Initial logistic regression modeling was performed using the glm function in the base R software to produce a regression model that was subjected to a separate validation step.

For the computation of probability or severity of a lysosomal storage disorder: the demographics, laboratory tests, diagnoses, medications, and physical exam records of 5,729 patients having received enzyme-proven diagnosis of Fabry's disease 224 distinct U.S.-based health care institutions between 1 Jan. 2000 and 31 Oct. 2015 were retrieved from a de-identified, secondary-use-consented, EHR-derived, HIPAA-compliant data warehouse (Cerner Health Health Facts® data warehouse). The retrieval encompassed more than 500 laboratory tests, 23 vital signs and flowsheet observation types, and more than 900 medication types as input variables for classification and predictive analysis. Corresponding records for an age-gender matched set of 6,102 control patients incident upon the same 224 institutions during the same time interval were also extracted. A support vector machine (SVM) method, such as described in method 200, was used to identify a subset of the input variables, including 9 laboratory tests, that were statistically significantly associated with the diagnosis of the sphingolipidosis condition (in the reduction-to-practice example, Fabry's disease).

To validate the regression model, records of 44 newly-incident enzyme-proven Fabry's disease patients whose care commenced at 22 distinct facilities between 1 Nov. 2015 and 31 Oct. 2016 were retrieved. Corresponding records for 56 age—gender matched control patients incident upon the same 22 institutions during the same time interval were also extracted. Owing to the small number of patients in the validation cohort, conventional logistic regression was not practical and therefore a Markov Chain Monte Carlo (MCMC) Bayesian method (metrop function in the MCMC R package) was used to perform confirmatory logistic regression. The MCMC Bayesian logistic regression was successful and produced stable results with 1,000 MCMC iterations. Bayes Information Criterion (BIC) and model regression coefficients did not differ significantly from the initial model. FIGS. 4A and 4B depict aspects of the statistical performance of this example embodiment actually reduced to practice using this clinical dataset, including a ROC curve (FIG. 4A) and statistical performance measures (FIG. 4B).

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure. Some example alternative embodiments include:

Embodiment 1: One or more computer-readable storage devices storing computer-useable instructions that, when used by one or more computing devices, cause the one or more computing devices to perform a method comprising: identifying an electronic medical record associated with a human patient; generating a multi-variable logistic regression statistical model capable of calculating a probability of clinically significant sphingolipidoses; receiving input data from the medical record for the human patient; determining from the received input data set a multi-variable biomarker based on a set of physiological variables in the received input data comprising a plurality of: attribution of acroparesthesia, attribution of a plurality of comorbid conditions, proteinuria, reduced glomerular filtration rate or creatinine clearance, elevated erythrocyte sedimentation rate, increased prothrombin time or International Normalized Ratio (INR), decreased platelet count, increased mean platelet volume, increased red blood cell distribution width (RDW), and absolutely and/or relatively increased monocytes in a WBC differential count; determining a probability of clinically significant sphingolipidoses for the human patient based on the multi-variable biomarker and the multi-variable logistic regression statistical model; modifying the electronic medical record according to the determined probability and to include data indicating that the member associated with the medical record is a candidate for receiving additional treatment or diagnostic procedures associated with sphingolipidoses; and based on the probability of clinically significant sphingolipidoses for the human patient, determined from the multi-variable biomarker and the multi-variable logistic regression statistical model, initiating an intervention action, the intervention action comprising one or more of modifying treatment of the patient, ordering additional diagnostics for the patient, scheduling treatment or diagnostics for the patient, and issuing a notification to a caregiver associated with the patient, wherein multi-variable biomarker is used by the multi-variable logistic regression statistical model.

Embodiment 2: Embodiment 1, wherein a plurality of comorbid conditions includes at least three comorbid conditions.

Embodiment 3: Embodiment 2, wherein the comorbid conditions include: splenomegaly, hypohidrosis or anhidrosis, hyperhidrosis, recurrent fevers, angiokeratoma, cornea *verticillata*, vertigo, headache, abdominal pain, diarrhea, constipation, early satiety or anorexia, tinnitus, left ventricular hypertrophy, hypertrophic cardiomyopathy, and/or prolonged QRS interval or shortened PR interval or low voltage on electrocardiogram as a composite variable.

Embodiment 4: A method of determining the presence, identity, and/or severity of a disease or condition in an individual, where the disease or condition is associated with abnormal glycan biosynthesis, degradation, or accumulation, the method comprising: (a) generating a biomarker as a probability or score emitted by a logistic regression model, wherein the independent variables referenced in said logistic regression model comprise: attribution of acroparesthesia, attribution of a plurality of conditions splenomegaly, hypohidrosis or anhidrosis, hyperhidrosis, recurrent fevers, angiokeratoma, cornea *verticillata*, vertigo, headache, abdominal pain, diarrhea, constipation, early satiety or anorexia, tinnitus, left ventricular hypertrophy, hypertrophic cardiomyopathy, and/or prolonged QRS interval or shortened PR interval or low voltage on electrocardiogram as a composite variable, proteinuria, reduced glomerular filtration rate or creatinine clearance, elevated erythrocyte sedimentation rate, increased prothrombin time or International Normalized Ratio (INR), decreased platelet count, increased mean platelet volume, increased red blood cell distribution width (RDW), and absolutely and/or relatively increased monocytes in a WBC differential count; and (b) correlating the magnitude of the biomarker with the presence, identity, and/or severity of the disease or condition for determining the presence, identity, and/or severity of the disease or condition; wherein the disease or condition is a lipidosis; wherein the sphingolipidosis is a lysosomal storage disease; wherein when the lysosomal storage disease is a gangliosidosis; and wherein the gangliosidosis is Fabry's Disease (alpha-galactosidase A deficiency).

Embodiment 5: Embodiment 4, wherein the multi-variable logistic regression statistical model is generated using a support vector machine, gradient boosting, or other machine-learning means to reduce the initial dimensionality of the statistical analysis.

Embodiment 6: Any of Embodiments 4-5, wherein the method further comprises determining one or more risk levels associated with the probability or severity of said lysosomal storage disorder in a human patient.

Embodiment 7: Any of Embodiments 4-6, wherein the method further comprises communicating for presentation to a clinician the one or more risk levels.

Embodiment 8: Any of Embodiments 4-7, wherein the method further includes communicating the electronic medical record to a clinician, where electronic medical record indicates the probability or severity of said lysosomal storage disorder in a human patient.

Embodiment 9: A method for screening for the presence, identity, and/or severity of a lysosomal storage disorder in a human patient, comprising: generating a multi-variable logistic regression statistical model capable of calculating a probability or severity of said lysosomal storage disorder using a plurality of variables; receiving an input data set for a human patient based on laboratory test results for the patient, the data set including a time associated with the test results, the test results determined from measurements that may be received at multiple measurement-session times; determining a probability or severity of said lysosomal storage disorder based on the input data set and the multi-variable logistic regression statistical model: modifying an electronic medical record associated with the patient according to the determined probability indicating that the patient is or is not a candidate for additional diagnostic testing and treatment; and, based on the probability or severity of said lysosomal storage disorder for the human patient determined from the input data set and the multi-variable logistic regression statistical model, initiating an intervention, the intervention comprising undertaking additional diagnostic or prognostic enzymatic or genetic testing directed to one or more specific lysosomal storage disorders.

Embodiment 10: Embodiment 9, wherein the multi-variable logistic regression statistical model is generated using a support vector machine, gradient boosting, or other machine-learning means to reduce the initial dimensionality of the statistical analysis.

Embodiment 11: Any of Embodiments 9-10, wherein the method further comprises determining one or more risk levels associated with the probability or severity of said lysosomal storage disorder.

Embodiment 12: Any of Embodiments 9-11, wherein the method further comprises communicating for presentation to a clinician the one or more risk levels.

Embodiment 13: Any of Embodiments 9-12, further comprising communicating the electronic medical record to a clinician, where electronic medical record indicates the probability or severity of said lysosomal storage disorder.

Embodiment 14: Any of Embodiments 9-13, wherein the probability comprises a multi-variable predictive score calculated using the multi-variable logistic regression statistical model, therein the multi-variable logistic regression statistical model is capable of calculating a probability or severity of said lysosomal storage disorder.

Embodiment 15: Any of Embodiments 9-14, wherein the multi-variable logistic regression statistical model employs a multi-variable support vector machine, gradient boosting, or other machine-learning means to reduce the initial dimensionality of the statistical analysis.

Embodiment 16: Any of Embodiments 9-15, wherein one or more risk levels are identified based on the probability or severity of said lysosomal storage disorder.

Embodiment 17: Any of Embodiments 9-16, wherein the one or more risk levels are presented to a clinician via an electronic medical record software system or device.

Embodiment 18: Any of Embodiments 9-17, wherein the intervention is identified based on the one or more risk levels.

It will be understood that certain features and subcombinations are of utility and may be employed without reference to other features and subcombinations and are contemplated within the scope of the claims. Not all steps listed in the various figures need be carried out in the specific order described. Accordingly, the scope of the technology is intended to be limited only by the following claims.

What is claimed is:

1. A computerized method of initiating an intervention action for sphingolipidosis, the method comprising:
    determining a multi-variable composite biomarker pattern of conditions or clinical events associated with an individual that is received as input data, the multi-variable composite biomarker pattern comprising two or more of: reduced glomerular filtration rate below a corresponding normal range, elevated erythrocyte sedimentation rate above a corresponding normal range, increased prothrombin time above a corresponding normal range, International Normalized Ratio (INR) above a corresponding normal range, mean platelet volume above a corresponding normal range, red blood cell distribution width (RDW) above a corresponding normal range, and absolutely or relatively increased monocytes in a WBC differential count above a corresponding normal range;
    training a multi-variable logistic regression statistical model to determine a probability of a clinically significant sphingolipidosis, the multi-variable logistic regression statistical model being trained with data from an anonymized data warehouse of electronic medical record (EMR) data that is collected via an automated process, the anonymized data corresponding to at least one or more patients other than the individual;
    applying the trained multi-variable logistic regression statistical model to the multi-variable composite biomarker pattern determined for the individual to determine the probability of the clinically significant sphingolipidosis for the individual; and
    based on the probability of clinically significant sphingolipidosis for the individual, automatically modifying treatment of the individual, ordering additional diagnostics for the individual, or scheduling treatment or diagnostics for the individual, wherein the individual is treated for sphingolipidosis based at least on the probability of clinically significant sphingolipidosis,
    wherein the method is executed by at least one device including a hardware processor.

2. The method of claim 1, wherein the multi-variable composite biomarker pattern further comprising a plurality of comorbid conditions, the plurality of comorbid conditions includes at least three comorbid conditions selected from splenomegaly, hypohidrosis or anhidrosis, hyperhidrosis, recurrent fevers, angiokeratoma, cornea *verticillata*, vertigo, headache, abdominal pain, diarrhea, constipation, early satiety or anorexia, tinnitus, left ventricular hypertrophy, hypertrophic cardiomyopathy, and prolonged QRS interval or shortened PR interval or low voltage on an electrocardiogram.

3. The method of claim 1, wherein the multi-variable logistic regression statistical model is generated using a machine learning technique, and wherein the machine learning technique is support vector machine or gradient boosting.

4. The method of claim 1, further comprising comparing the probability of clinically significant sphingolipidosis to a diagnostic threshold, wherein the diagnostic threshold is part of a set of diagnostic thresholds that indicate a presence, identity, or severity of clinically significant sphingolipidosis, and wherein initiating the intervention action is further based on comparing the probability to the diagnostic threshold.

5. The method of claim 1, wherein the input data is received from an EMR associated with the individual.

6. The one or more computer-readable storage devices of claim 1, wherein the input data is received from an EMR associated with the individual.

7. The method of claim 1, wherein the multi-variable composite biomarker pattern comprises at least three of the following: increased prothrombin time above a corresponding normal range, International Normalized Ratio (INR) above a normal range, mean platelet volume above a normal range, red blood cell distribution width (RDW) above a normal range, and absolutely or relatively increased monocytes in a WBC differential count above a corresponding normal range.

8. The method of claim 1, wherein ordering additional diagnostics for the individual and scheduling treatment or diagnostics for the individual are automatically performed based on the probability of clinically significant sphingolipidosis for the individual.

9. One or more computer-readable storage devices storing computer-useable instructions that, when used by one or more computing devices, cause the one or more computing devices to perform a method of initiating an intervention action for sphingolipidosis, the method comprising:
    determining a multi-variable composite biomarker pattern of conditions or clinical events associated with an individual that is received as input data, the multi-variable composite biomarker pattern comprising two or more of: reduced glomerular filtration rate below a corresponding normal range, elevated erythrocyte sedimentation rate above a corresponding normal range, increased prothrombin time above a corresponding normal range, International Normalized Ratio (INR) above a corresponding normal range, mean platelet volume above a corresponding normal range, red blood cell distribution width (RDW) above a corresponding normal range, and absolutely or relatively increased monocytes in a WBC differential count above a corresponding normal range;

training a multi-variable logistic regression statistical model to determine a probability of a clinically significant sphingolipidosis, the multi-variable logistic regression statistical model being trained with data from an anonymized data warehouse of electronic medical record (EMR) data that is collected via an automated process, the anonymized data corresponding to at least one or more patients other than the individual;

applying the trained multi-variable logistic regression statistical model to the multi-variable composite biomarker pattern determined for the individual to determine the probability of the clinically significant sphingolipidosis for the individual; and based on the probability of clinically significant sphingolipidosis for the individual, automatically modifying treatment of the individual, ordering additional diagnostics for the individual, or scheduling treatment or diagnostics for the individual, wherein the individual is treated for sphingolipidosis based at least on the probability of clinically significant sphingolipidosis.

10. The one or more computer-readable storage devices of claim 9, wherein the multi-variable logistic regression statistical model is generated using a machine learning technique.

11. The one or more computer-readable storage devices of claim 10, wherein the machine learning technique is support vector machine or gradient boosting.

12. The one or more computer-readable storage devices of claim 9, further comprising comparing the probability of clinically significant sphingolipidosis to a diagnostic threshold, wherein the diagnostic threshold is part of a set of diagnostic thresholds that indicate a presence, identity, or severity of clinically significant sphingolipidosis.

13. The one or more computer-readable storage devices of claim 12, wherein initiating the intervention action is further based on comparing the probability to the diagnostic threshold.

14. The one or more computer-readable storage devices of claim 9, further comprising determining a risk level of clinically significant sphingolipidosis based on comparing the probability to the diagnostic threshold, and communicating the risk level as part of the notification.

15. One or more computer-readable storage devices storing computer-useable instructions that, when used by one or more computing devices, cause the one or more computing devices to perform a method of initiating an intervention action for sphingolipidosis, the method comprising:

identifying an EMR associated with an individual;

receiving a multi-variable logistic regression statistical model generated to determine a probability of clinically significant sphingolipidosis;

receiving input data from the EMR associated with the individual;

determining a multi-variable composite biomarker pattern of conditions or clinical events associated with an individual that is received as input data, the multi-variable composite biomarker pattern comprising two or more of: reduced glomerular filtration rate below a corresponding normal range, elevated erythrocyte sedimentation rate above a corresponding normal range, increased prothrombin time above a corresponding normal range, International Normalized Ratio (INR) above a corresponding normal range, mean platelet volume above a corresponding normal range, red blood cell distribution width (RDW) above a corresponding normal range, and absolutely or relatively increased monocytes in a WBC differential count above a corresponding normal range;

training a multi-variable logistic regression statistical model to determine a probability of a clinically significant sphingolipidosis, the multi-variable logistic regression statistical model being trained with data from an anonymized data warehouse of electronic medical record (EMR) data that is collected via an automated process, the anonymized data corresponding to at least one or more patients other than the individual;

applying the trained multi-variable logistic regression statistical model, to the multi-variable composite biomarker pattern determined for the individual, to determine the probability of the clinically significant sphingolipidosis for the individual; and based on the probability of clinically significant sphingolipidosis for the individual, automatically modifying treatment of the individual, ordering additional diagnostics for the individual, or scheduling treatment or diagnostics for the individual, wherein the individual is treated for sphingolipidosis based at least on the probability of clinically significant sphingolipidosis.

16. The one or more computer-readable storage devices of claim 15, the method further comprising modifying the EMR according to the determined probability to include data indicating that the individual associated with the EMR is a candidate for receiving additional treatment or diagnostic procedures associated with sphingolipidosis.

17. The one or more computer-readable storage devices of claim 15, the method further comprising comparing the probability of clinically significant sphingolipidosis to a diagnostic threshold.

18. The one or more computer-readable storage devices of claim 17, wherein the diagnostic threshold is part of a set of thresholds that indicate a presence, identity, or severity of clinically significant sphingolipidosis.

19. The one or more computer-readable storage devices of claim 15, the method further comprising determining a risk level of clinically significant sphingolipidosis based on comparing the probability to the diagnostic threshold, and communicating the risk level as part of the notification.

20. The one or more computer-readable storage devices of claim 15, wherein initiating the intervention action is further based on comparing the probability to the diagnostic threshold.

21. The one or more computer-readable storage devices of claim 15, wherein the plurality of comorbid conditions includes at least three comorbid conditions.

22. The one or more computer-readable storage devices of claim 21, wherein the multi-variable composite biomarker pattern further includes a plurality of comorbid conditions, the plurality of comorbid conditions includes at least three comorbid conditions selected from: splenomegaly, hypohidrosis or anhidrosis, hyperhidrosis, recurrent fevers, angiokeratoma, cornea *verticillata*, vertigo, headache, abdominal pain, diarrhea, constipation, early satiety or anorexia, tinnitus, left ventricular hypertrophy, hypertrophic cardiomyopathy, and prolonged QRS interval or shortened PR interval or low voltage on electrocardiogram.

\* \* \* \* \*